United States Patent [19]
Iversen et al.

[11] Patent Number: 5,961,552
[45] Date of Patent: Oct. 5, 1999

[54] INTERNALLY CONFIGURED PROSTHESIS

[75] Inventors: Alfred A. Iversen, Wayzata; Stephen M. Trinter, Eden Prairie, both of Minn.

[73] Assignee: PMT Corporation, Chanhassen, Minn.

[21] Appl. No.: 08/921,906

[22] Filed: Aug. 2, 1997

[51] Int. Cl.⁶ .............................. A61F 2/12; A61F 2/02
[52] U.S. Cl. ...................................... 623/8; 623/7
[58] Field of Search ........................ 623/7, 8, 11

[56] References Cited

U.S. PATENT DOCUMENTS

| | | | |
|---|---|---|---|
| 3,366,975 | 2/1968 | Pangman | 623/8 |
| 3,559,214 | 2/1971 | Pangman | 623/8 |
| 3,683,424 | 8/1972 | Pangman | 623/8 |
| 4,205,401 | 6/1980 | Frisch | 623/8 |
| 4,676,795 | 6/1987 | Grundei | 623/8 |
| 4,955,909 | 9/1990 | Ersek et al. | 623/8 |
| 5,158,571 | 10/1992 | Picha | 623/8 |
| 5,171,269 | 12/1992 | Bark | 623/8 |
| 5,383,929 | 1/1995 | Ledergerber | 623/8 |
| 5,525,275 | 6/1996 | Iversen et al. | 623/8 X |
| 5,534,023 | 7/1996 | Henley | 623/8 |
| 5,545,217 | 8/1996 | Offray et al. | 623/8 |
| 5,549,671 | 8/1996 | Waybright et al. | 623/11 X |
| 5,658,330 | 8/1997 | Carlisle et al. | 623/8 X |

FOREIGN PATENT DOCUMENTS

0 178 483  4/1986  European Pat. Off. ................... 623/8

*Primary Examiner*—David H. Willse
*Assistant Examiner*—Suzette J. Jackson
*Attorney, Agent, or Firm*—Anthony G. Eggink; Jeffery L. Cameron

[57] ABSTRACT

An improved mammary prosthesis for implantation in humans comprising: a soft, flexible outer membrane forming an enclosure for receiving a filler material; an enhanced, undulating, random sculptured, irregular, substantially smooth surface of peaks, valleys, slopes and terraces without interstices disposed over at least a portion of said outer membrane; an internal structure within said membrane for supporting said outer membrane and providing an enhanced, life-like look and feel to the prosthesis; and a soft, partially-deformable, elastic filler material received within said outer membrane and cooperating with said internal structure to support said outer membrane.

37 Claims, 5 Drawing Sheets

INTERNALLY CONFIGURED PROSTHESIS

BACKGROUND OF THE INVENTION

It is well known in the field of plastic surgery to enlarge the female breast or replace other body organs or structures with prostheses which are surgically implanted therein. With respect to female breasts, in many instances it becomes necessary to remove the entire mammary gland or a substantial portion thereof as a result of cancerous infection or other disease. The surgical removal of the diseased body tissue leaves voids which may be filled by such a prosthetic implant. Such implants provide physical support for the surrounding body tissue and organs and in the case of voids near the skin, preserve the outward appearance of the body. When cancerous, pre-cancerous, or damaged tissue is removed, it is often possible to insert the prosthesis to be implanted through the same surgical incision used for removing the tissue. Particularly in the cases where a radical removal of tissue has occurred it is desirable to use an implant for the purpose of restoring the human body to its original normal form. The restoration of the normal appearance of the body has an extremely beneficial psychological effect on post-operative patients, eliminating much of the shock and depression that often follows extensive surgical procedures.

Among the various problems involved in prosthetic implants are those of preserving the natural shape and feel of the body over time after implantation. Some earlier implants comprise an outer layer of sponge material which retains a relatively natural softness and resiliency similar to the replaced body tissue. However, the inherent porosity of such sponge material has also been a source of considerable inconvenience and disappointment because the sponge eventually becomes invaded with connective tissue, sometime called capsule formation, throughout all or a major portion of the implant. The connective tissue, being fibrous, shrinks as it ages, sometimes called capsular contraction, resulting in the compression of the implant thereby causing the implant to lose both its original size and shape and its original resiliency. Cases are known in which the shrinkage has been as much as 20 to 30% of the original size. These changes in shape, size and resiliency may be distressing and embarrassing to the patient and are obviously undesirable.

Implantable devices, particularly breast implants, prosthesis and tissue expanders, are generally known. Many of these devices include a sack-like or envelope-like bladder which is manufactured from an elastomeric material such as silicone rubber and then filled with a liquid or gel. The liquid or gel filling can be a silicone fluid or a saline solution. A combination of an elastomeric envelope and liquid or gel fill material is utilized to imitate properties of the tissue being replaced or supplemented in breast implants. However, simple fillers of silicone or saline have not provided a totally life-like look and feel to the prosthesis. An expander may be an expandable bladder with a local or remote port to add or remove liquid or gel. In tissue expanders, the same general design allows variable degrees of expansion.

Initially developed soft pliable prosthetic implants included a smooth surface. It was felt that the smooth surface would elicit a minimal foreign body reaction. This was found to be true, however, the smooth surface prevented attachment of the scar capsule to the prosthesis so that any movement of the host created a shearing effect which lead to a later and perhaps more severe encapsulation response if the prosthesis was subject to trauma or some sort of infection in the area of implant.

Picha, in U.S. Pat. No. 5,002,572, discloses that it is known that the implantation of an article or material into soft tissue initiates a sequence of physiological events in which the body attempts to remove or isolate the foreign entity. The presence of an implant may lead to the formation of a collagen layer of increased density as part of the host's attempt to isolate the foreign body. Such layers are referred to as the "fibrous capsule" and its formation is dependent upon a multiplicity of factors including surgical procedure, implant shape and size, relative movement between and surrounding tissue, and surface morphology of the implant or texture.

Picha discloses an implant in which the surface of the device in tissue contact is molded to provide a regular pattern of micropillars at least 100 microns ($\mu$m) in height with transverse dimensions and interpillar spacing each no greater than 5000 microns. Picha discloses that micropillars have been found to influence the density, vascularity, and cellularity of the capsule surrounding the implant.

Ersek et al, in U.S. Pat. No. 4,955,909, disclose that capsular contracture causing firmness of soft silicone implants is a serious problem that may result from several causative factors that have, as their final pathway, the development of increased scar tissue. Ersek et al. state that this problem may be reduced by forming a net-like three-dimensional grid on the silicone surface in order to gain fibroblast ingrowth into the interstices and thus prevent micromotion at the host prosthesis interface.

G. Picha and D. Siedlak, in "Ion-Beam Microtexturing of Biomaterials", *MD and DI* pp. 39–42 (April, 1984), disclose a method to manufacture uniform pillar projections on the surface of an implant using ion-beam thruster technology. Although this method overcomes the disadvantages of the open cell method (discussed below), it is believed a costly process and uneconomical to apply to custom-shaped surfaces.

Figure 4:
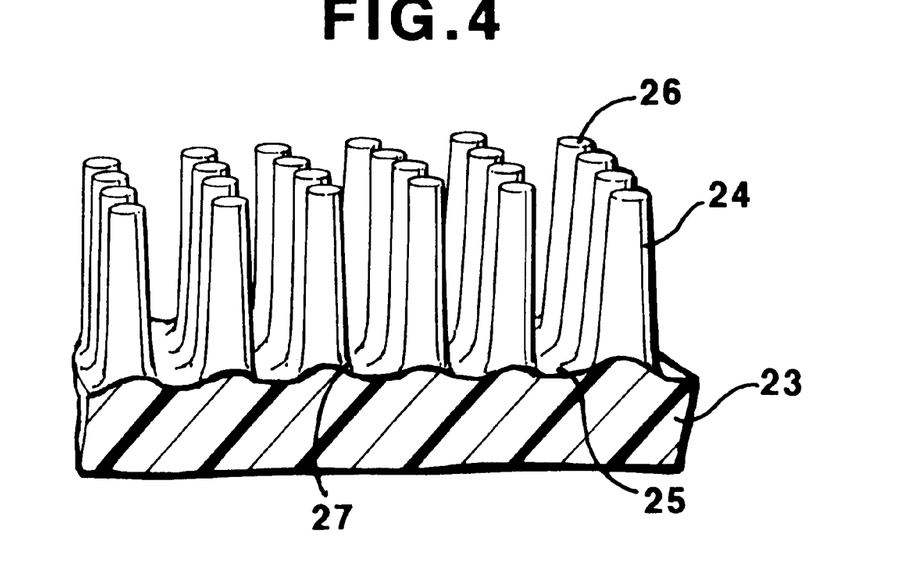
FIG. 4 is a greatly enlarged cross-sectional view of the regular textured surface of a prior art implant surface.

The pillar surface structure of Picha '572, Ersek et al '909 and Picha and Siedlak ion-beamed surfacing technology is generally depicted in FIG. 4.

Figure 5:
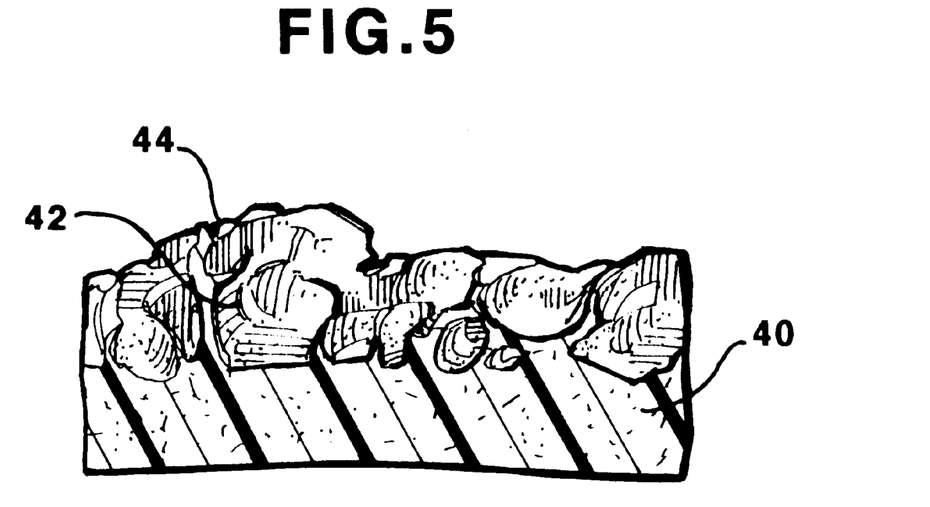
FIG. 5 is a greatly enlarged cross-sectional view of a prior art open-celled, textured surface.
Figure 6:
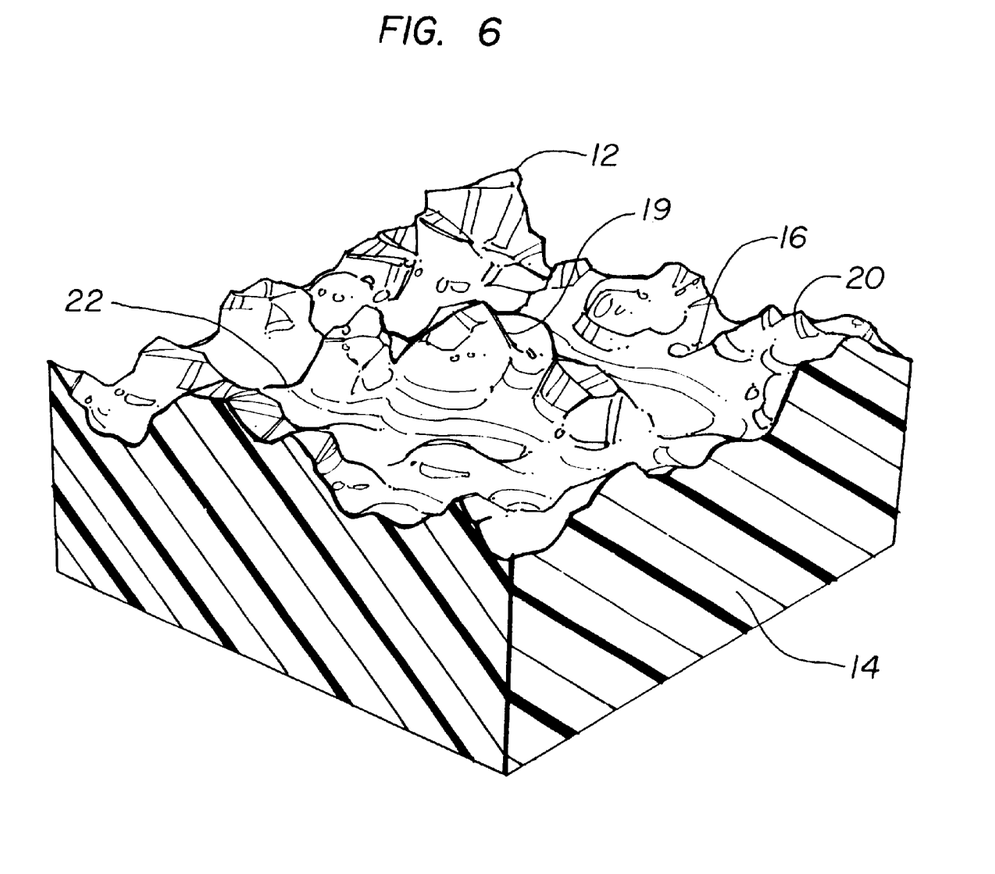
FIG. 6 is a greatly enlarged perspective view of the contoured enhanced surface.

In U.S. Pat. No. 4,889,744, issued to Quaid, a method for making a medical implant with an open cell textured surface is disclosed. The implant has an open cell texture produced by applying soluble particles (e.g., salt, sugar, etc.) to an uncured layer of silicone dispersion. The silicone layer is then fully cured. Subsequent to curing, the silicone layer is then placed in a suitable solvent so that the solid particles are dissolved from the surface of the shell. This method creates open cells on the surface of the implantable body. This prior art device is depicted in FIG. 5.

The open cell structure manufacturing technique is believed to pose three potential problems. First, introduction of a foreign or non-silicone particle to the surface of the uncured silicone can affect the properties of the silicone during the curing process or over the life of the implant. The open cell structure also creates potential silicone fragments which can easily become detached from the open cell structure or cell wall as can be readily seen by the physical shape of the cells in FIG. 5. Finally, use of a soluble particle requires that the particle be fully dissolved prior to implant. If the particle is not fully dissolved or the particle becomes encapsulated by the silicone, such particles may be released from the surface after implantation. This may be detrimental.

Thus, it is generally known to alter the surface morphology or topology of an implantable device to improve the host prosthesis interface. It will also be appreciated that the selection of an altered surface configuration requires balancing between having sufficient texturing to provide adequate anchoring of the implant and having a textured design which minimizes adverse body reaction. Thus, the ideal implant provides sufficient anchoring while minimizing the encapsulation response and subsequent scar tissue.

Other considerations in selecting the technology for altering or texturing the implantable device include the cost of the method, along with any potential hazards the method may create in the final implantable device. As was seen with the open cell textured method, the potential for contamination from the soluble particles or fragmentation of a cell wall may pose a problem. Further, the ion-beam thruster method may be considered uneconomical.

Accordingly, a need exists for an improved or enhanced implant surface morphology or topology which provides sufficient anchoring at the host prosthesis interface while minimizing the reaction of the human body to the foreign body implant. Further, a method to manufacture such enhanced surface is needed. The selected implant enhanced surface should also have a closed cell structure without interstices which is economically manufactured. The present invention addresses these needs as well as other problems associated with existing textured surface implants. The present invention also offers further advantages over the prior art and solves other problems associated therewith.

In addition to problems of capsular contraction, previous prostheses did not have the same look and feel, when implanted, as the removed tissue.

There is a need for a mammary prosthesis with an improved filler material which gives a more life-like look and feel to the prosthesis.

There is also a need for a mammary prosthesis with an internal structure which gives the prosthesis a more life-like look and feel than previous prostheses.

SUMMARY OF THE INVENTION

An improved mammary prosthesis for implantation in humans comprising: a soft, flexible outer membrane forming an enclosure for receiving a filler material; an enhanced, undulating, random sculptured, irregular, substantially smooth surface of peaks, valleys, slopes and terraces without interstices disposed over at least a portion of said outer membrane; an internal structure within said membrane for supporting said outer membrane and providing an enhanced, life-like look and feel to the prosthesis; and a soft, partially-deformable, elastic filler material received within said outer membrane and cooperating with said internal structure to support said outer membrane.

The implant or prosthesis of the present invention includes an undulating sculptured surface disposed over at least a portion of the outer membrane surface. The undulating enhanced surface is characterized by a random or irregular distribution of peaks separated by valleys. The peaks and valleys have gradual contoured slopes and terraces therebetween.

The undulating enhanced surface is further characterized by generally smooth transitions between peaks and valleys. The transitions are substantially free of indentations which may trap body fluids. The undulating surface provides improved anchoring of the implant, yet reduces host reaction.

The enhanced surface implantable body can include an outer membrane forming an enclosure for receiving a filler material. The filler material may be included in the implant when purchased or may be added later through a fill port. The filler material may be a fluid or gel, but is preferably a soft, partially-deformable, elastic material. Possible fluids are: saline, silicone, silicone gel, hydrogels, triglycerides, and other biocompatible materials.

The soft, partially-deformable, elastic material is preferably selected from the group consisting of sponge rubber, foam rubber, silicone beads, silicone sponge, open cell foam, and silicone fibers in fluid suspension. However, any other equivalent soft, partially-deformable, elastic material may be used to provide an enhanced life-like look and feel to the prosthesis.

In a preferred embodiment, the mean peak to valley height differential may illustratively be 800 $\mu$m to 2500 $\mu$m (0.03" to 0.100"). The spacing between peaks may be 100 $\mu$m to 600 $\mu$m (0.004" to 0.024"). Further, the entire outer membrane surface can have disposed thereon the undulating enhanced surface. The smooth transitions between peaks and valleys can further include terraced contours and slopes. The undulating textured surfaces are preferably free of open cells.

The sculptured enhanced surface of the present implant is formed by first providing an elastomeric material suitable for use as an implant which has a tacky surface. This material may be an uncured silicone rubber. The silicone rubber may be dispersed in a solvent and applied to a mandrel.

Cured polymeric particles are randomly deposited on the tacky surface to form an intermediate textured surface. The cured polymeric particles may be silicone particles which are ground to a specific size, preferably under cryogenic conditions. The polymeric particles in a preferred method have an average diameter of 300 $\mu$m to 600 $\mu$m (0.012" to 0.024"). It is recognized however, that the size and distribution of particles may be varied with resulting variations in the degree of surface enhancement. Further, the quantity of polymeric particles which are deposited on the tacky surface will also affect the surface enhancement.

The tacky surface having the deposited random distribution of cured polymeric particles, the intermediate enhanced surface, is then cured. Curing of this surface includes heating the material to a temperature between 130° F. and 270° F. for approximately one hour.

A layer of uncured elastomeric material, suitably on a mandrel, is then applied over the intermediate textured surface after it has been cured. The uncured elastomeric material is preferably a silicone rubber dispersed in a solvent into which the mandrel is dipped.

Upon applying the layer of uncured elastomeric material, the intermediate enhanced surface having the layer applied thereon is cured to form the undulating sculptured, irregular enhanced surface. Curing of the intermediate enhanced surface having the applied layer of uncured elastomeric material includes heating to a temperature between 130° F. and 270° F. for approximately one hour.

An object and advantage of the present invention is that it provides an improved filler material which provides a more life-like look and feel to the prosthesis. The filler material is a soft, partially-deformable, elastic material.

Another object and advantage of the present invention is that it provides an internal structure within the prosthesis which supports the outer membrane of the prosthesis and cooperates with the improved filler material to provide a more life-like look and feel.

Another object and advantage of the present invention is that it provides an enhanced, undulating, random sculptured, irregular, substantially smooth surface of peaks, valleys, slopes and terraces without interstices which solves many of the problems with capsular contraction found in earlier prostheses.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

As required, detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the present invention.

Figure 1:
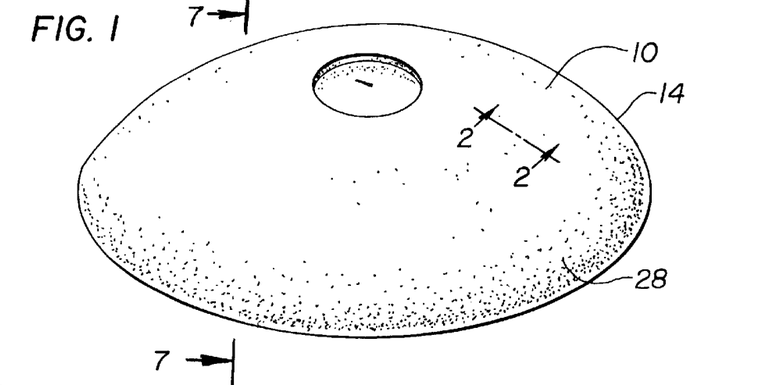
FIG. 1 is a perspective view of an implant having an undulating enhanced surface of the present invention.

FIG. 1 is a perspective view of an improved mammary prosthesis 10 which may or may not be expandable. The improved mammary prosthesis 10 includes an outer membrane 14 which forms an enclosure 28 for receiving a filler material. A filler material may be added to the membrane prior to or during surgery.

Figure 2:
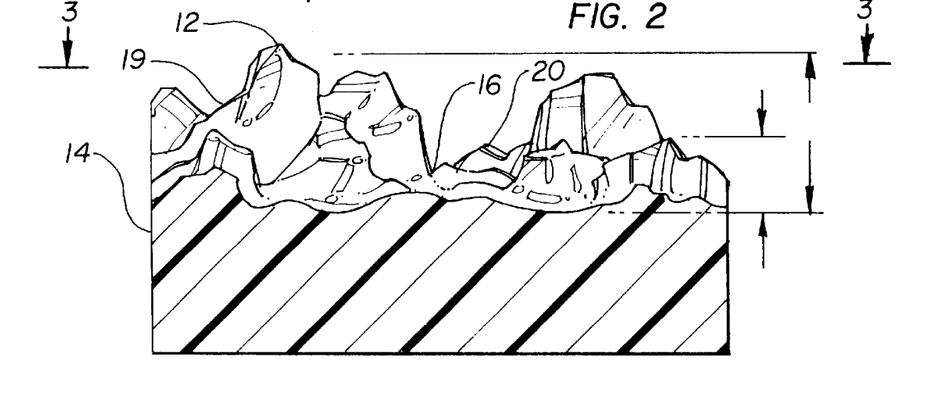
FIG. 2 is a greatly enlarged cross-sectional view taken along a line 2—2 of FIG. 1, illustrating the enhanced surface.

FIG. 2 is a greatly enlarged cross-sectional view of the outer membrane along line 2—2 of FIG. 1. As depicted in FIG. 2, the cross-section includes a thickness of elastomeric material 14 exhibiting an enhanced surface 19. The surface 19 is an undulating sculptured surface which is disposed over at least a portion of the outer membrane surface. The undulating textured surface 19 is characterized by a random or irregular distribution of peaks 12 separated by valleys 16. The peaks 12 and valleys 16 are separated by gradual contoured slopes 20.

The undulating textured surface 19 is further characterized by generally smooth transitions between the peaks 12 and valleys 16. The transitions are substantially free of indentations, interstices or open cells, which may trap body fluids or cause irritation at the host prosthesis interface. Thus, the undulating surface 19 provides improved anchoring of the prosthesis 10 yet reduces host reaction.

Figure 3:
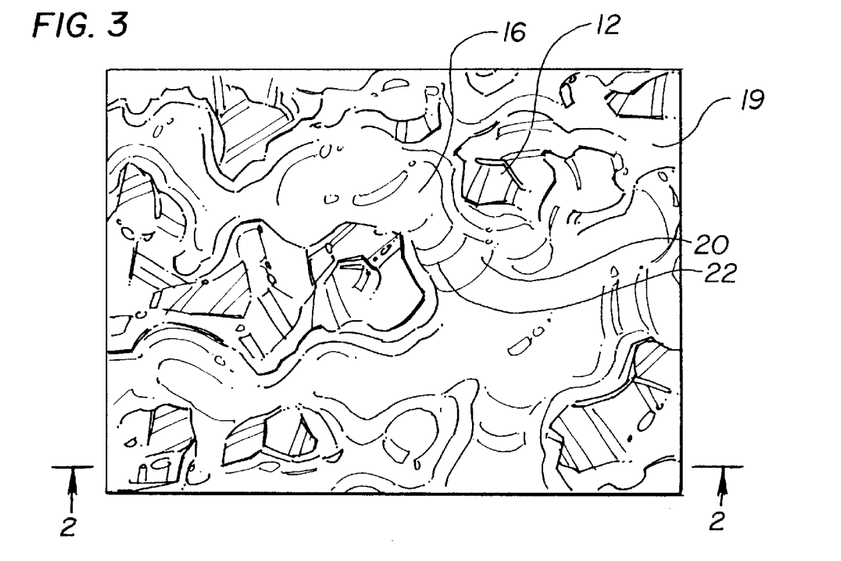
FIG. 3 is a greatly enlarged fragmentary top plan view taken along lines 3—3 of FIG. 2 showing the general shape of the contoured enhanced surface.

FIG. 3 illustrates a greatly enlarged fragmentary view of the enhanced surface 19 in plan view. The slopes 20 leading from peaks 12 to valleys 16 are depicted as contours 22 which are terraced along the transition between peaks 12 and valleys 16. This transition is generally smooth. Because the undulating enhanced surface 19 of the present invention is difficult to describe, FIGS. 4 and 5 have been included for comparison of the surface 19 topology or morphology of the present implant 10 with the surface achieved with prior art surface texturing methods as described above in the background.

FIG. 4 depicts a surface texture which includes a fixed array of pillars 32. As depicted, the membrane outer surface includes a layer of elastomeric material 30 on which pillars 32 are formed. The pillars 24 as characterized by sharp transitions 38 from valleys 34 and rise to plateaued peaks 36. As is clearly visible, the texture is designed to provide strong anchoring of the implant at the host prosthesis interface.

FIG. 5 depicts another prior art textured surface which is manufactured by placing soluble crystals on the uncured elastomeric material. Subsequent to curing, the soluble particles are dissolved to leave a texture surface. The prior art textured surface includes a layer of elastomeric material 40 on which the textured surface lies. The textured surface is characterized by void volumes or pits 42 which are formed by dissolving the crystals on the surface, such as sugar or salt. Thus, the surface is covered with pits and cavities which provide the means for anchoring the prosthesis at the host prosthesis interface. The peaks 44 generally include sharp or fragmentary edges with sharp transitions to valleys with open cells substantially covering the surface.

The preferred prosthesis 10 of the present invention includes mean peak 12 to valley 16 differentials ranging from 25 μm to 2540 μm (0.001" to 0.100") but ideally between 800 μm to 2500 μm (0.03" to 0.100"). Preferably, the entire outer surface has disposed thereon an undulating textured surface 19. The surface 19 is also substantially free of open cells.

The undulating surface 19 of the present invention may be formed by at least one process which assists in defining and understanding the enhanced surface 19. Generally, the process begins with providing an elastomeric material suitable for use in an implant which has a tacky surface. The preferred material is an uncured silicone rubber. The silicone is preferably dispersed in a solvent, as is commonly known, into which a forming mandrel is dipped.

A distribution of cured polymeric particles is then deposited on the tacky surface to form an intermediate textured surface. The polymeric particles are silicone particles which have been ground to a desired diameter and particle distribution. As discussed in the example below, the grinding is preferably completed cryogenically. The polymeric particles can have an average diameter that is in a range of 300 μm to 600 μm (0.012" to 0.024") but generally less than 500 μm (0.02").

The intermediate textured surface is then cured. The curing step includes heating to a temperature between 130° F. and 270° F. for about one hour.

A layer of uncured elastomeric material is applied over the intermediate textured surface. This material is again preferably dispersed in a solvent. The preferred uncured elastomeric material is uncured silicone rubber. This material is then cured to form the undulating enhanced surface 19. The step of curing the intermediate surface having the applied layer of uncured elastomeric material includes heating to a temperature of about 130° F. to 270° F. for about one hour.

The following method is offered illustratively and is not to be viewed as limiting. Other methods of manufacture may also achieve the enhanced surface 19 of the present invention.

EXAMPLE 1

Method of Producing a Textured Surface Implant

The following procedure was utilized to produce an implant with the textured or enhanced surface of the present invention:

1. Producing the Particulate
   a. Silicone feed material was placed in a grinding unit, suitable for cryogenic grinding.
   b. Liquid nitrogen was added to achieve a cryogenic state. Liquid nitrogen was added until the silicone was fully immersed in a bath of the nitrogen. Material was ground. The time required for sufficient grinding will vary depending on the amount of feed stock placed in the grinding unit.
   c. Step 1b was repeated.
   d. Ground material was dumped into a filtering sieve.
2. Filtering the Particulate
   a. The ground silicone was pushed around the sieve screen and the sides of the sieve were tapped to agitate the silicone which loosened the particles and allowed them to fall through the screen in to the collection bin. This was continued until most of the fine particles had been filtered from the feed and a sufficient amount was collected.
3. Dipping and Enhancing the Tissue Expander
   a. Holding the mandrel upside down, it was slowly dipped into uncured silicone dispersed in a solvent. Excess silicone was allowed to drip off the mandrel.
   b. The mandrel was then placed in an oven for approximately 12–15 minutes at 54° C. (130° F.). The mandrel was removed.
   c. If the dip appeared acceptable, steps 3a and 3b were repeated until proper thickness was obtained.
   d. The mandrel was then placed in the oven for 30 minutes at 54° C. (130° F.). The mandrel was removed and checked for defects such as contaminants, bubbles or tears. The mandrel was then placed in an oven for 30 minutes at 130° C. (266° F.).
   e. The mandrel was then removed from the oven and carefully placed in distilled water to cool.
   f. After mandrel had cooled, step 3a was repeated.
   g. The mandrel was placed in the oven for 2–3 minutes at 54° C. (130° F.) in order to set the silicone.
   h. The mandrel was then removed from the oven.
   i. Filtered particles from step 2a were shaken over the mandrel until the entire surface was fully covered.
   j. With an air compressor, held a blow gun approximately 1½ to 2 feet away from the enhanced mandrel. With a series of shots of air, blew off the excess silicone particles being careful not to upset the tacky, underlying silicone layer. Examined the mandrel to insure complete particulate coverage.
   k. The mandrel was placed in the oven for 30 minutes at 54° C. (130° F.). The mandrel was then placed in the oven for an additional 30 minutes at 130° C. (266° F.) to fully cure the silicone.
   l. Removed from the oven and gently placed the mandrel in distilled water to cool.
   m. After about 5 minutes, removed the mandrel from the water and wiped dry with a towel. This not only will dry the mandrel but will also remove some of the remaining excess particles.
4. Applying the Top Coat
   a. Repeated 3a, using a solvent thinned silicone and immediately placed the mandrel in a vacuum jar and removed the air from the jar. This helped to expel the small bubbles from the mandrel surface.
   b. After approximately 15–20 minutes in the vacuum jar, the mandrel is removed and placed it in the oven for 30–45 minutes at 54° C. (130° F.).
   c. Fully cured in the oven for 30 minutes at 130° C. (266° F.).

As shown in FIGS. 7A–7E, the improved mammary prosthesis 10 may preferably have a soft, partially-deformable, elastic filler material 30 received within the outer membrane 14 to support the outer membrane 14 and provide an enhanced life-like look and feel to the prosthesis.

The soft, partially-deformable, elastic material 30 is preferably selected from the group consisting of sponge rubber, foam rubber, silicone beads, and silicone fibers in fluid suspension. However, any other equivalent soft, partially-deformable, elastic material may be used to provide an enhanced life-like look and feel to the prosthesis.

Figure 7A:
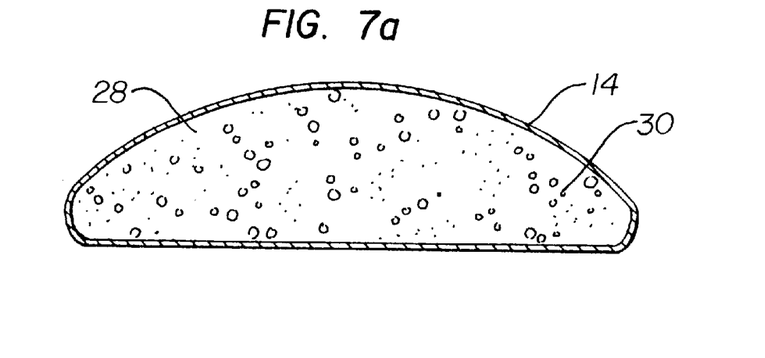
FIG. 7A is a cross-section along the lines 7 of FIG. 1 showing an embodiment having a filler material of sponge rubber or foam rubber.

FIG. 7A shows an embodiment in which the filler material 30 is sponge rubber or foam rubber 30A.

Figure 7B:
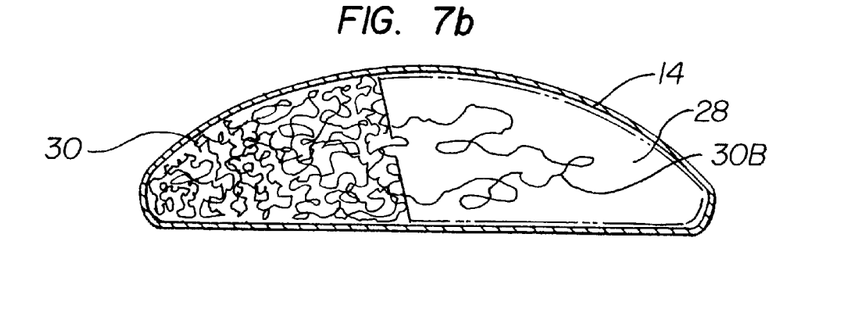
FIG. 7B is a cross-section along the lines 7 of FIG. 1 showing an embodiment having a filler material of silicone fibers dispersed in a fluid.

FIG. 7B shows an embodiment in which the filler material is silicone fibers 30B dispersed in a fluid.

Figure 7C:
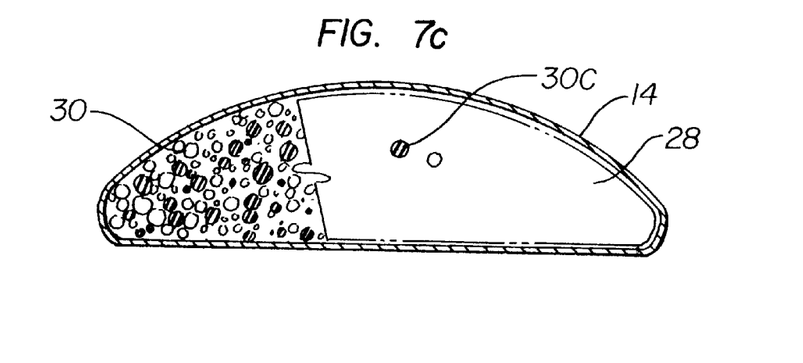
FIG. 7C is a cross-section along the lines 7 of FIG. 1 showing an embodiment having a filler material of silicone beads, which are solid or hollow randomized spheres.

FIG. 7C shows an embodiment in which the filler material is silicone beads 30C which are solid or hollow randomized spheres.

Figure 7D:
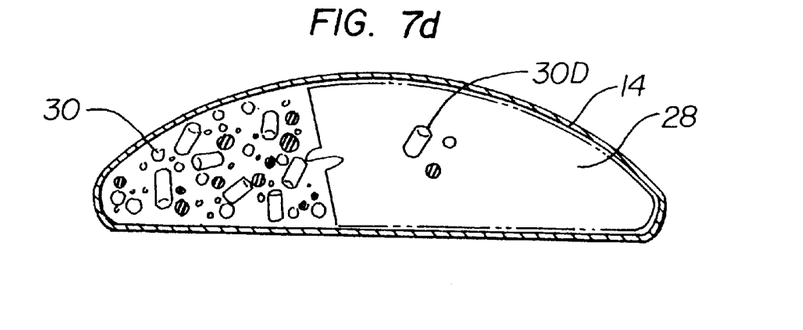
FIG. 7D is a cross-section along the lines 7 of FIG. 1 showing an embodiment having a filler material of silicone cylinders and solid or hollow spheres.

FIG. 7D shows an embodiment in which the filler material is silicone beads 30D which are cylinders and solid or hollow spheres.

Figure 7E:
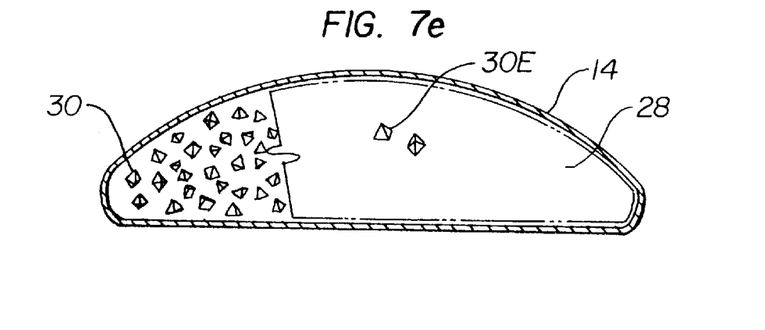
FIG. 7E is a cross-section along the lines 7 of FIG. 1 showing an embodiment having a filler material of fractured silicon pyramids and tetrahedrons.

FIG. 7E shows an embodiment in which the filler material is fractured silicone pyramids and tetrahedrons.

Figure 8:
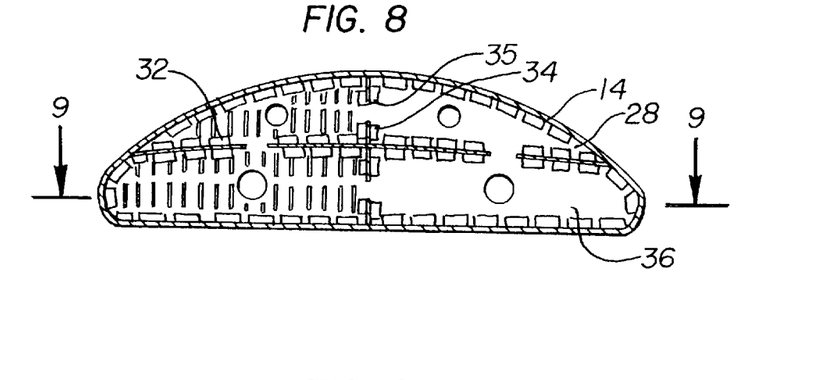
FIG. 8 is a cross-section along the lines 7 of FIG. 1 showing an embodiment having an internal structure consisting of baffles and louvers.
Figure 9:
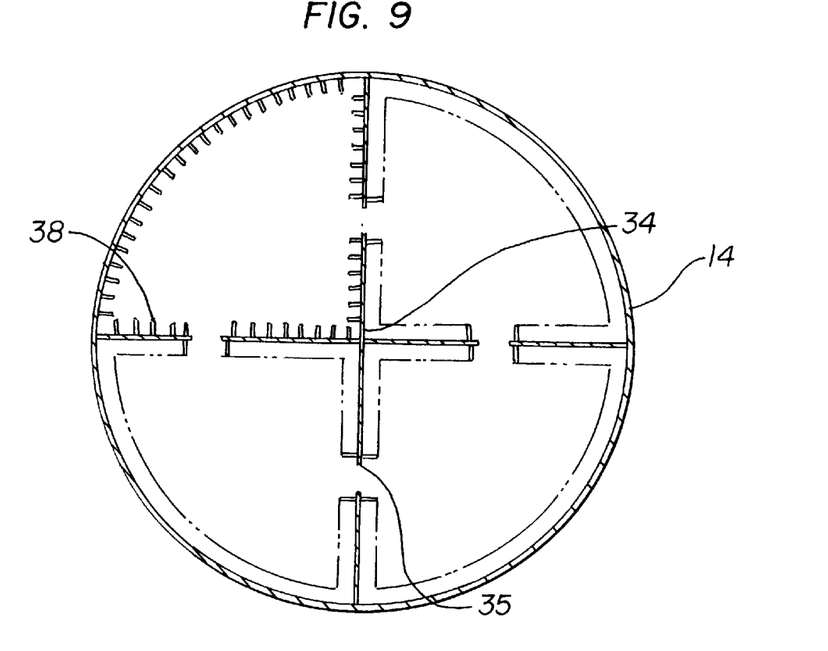
FIG. 9 is a cross-section along the lines 9 in FIG. 8.

FIG. 8 shows an embodiment in which the improved mammary prosthesis 10 further comprises an internal structure 32 within the outer membrane 14 for supporting the outer membrane 14 and providing an enhanced, life-like look and feel to the prosthesis 10. In the preferred embodiment, the internal structure 32 consists of a plurality of baffles 34 dividing the enclosure 28 into a plurality of compartments 36. The baffles 34 preferably have weep holes 35 which impede the movement of fluid between the compartments 36. The internal structure 32 also consists of a plurality of small louvers 38 which impede the movement of fluid within the compartments 36.

In some embodiments, the filler material 30 cooperates with the internal structure 32 to provide an enhanced, life-like look and feel to the prosthesis 10. For example, the compartments 36 may be filled with the filler material 30.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. An improved mammary prosthesis for implantation in humans comprising:
    (a) a soft, flexible outer membrane having front, rear, and side portions forming an enclosure for receiving filler material;
    (b) a soft, partially-deformable, elastic filler material within said outer membrane to support said outer membrane and provide an enhanced life-like look and feel to the prosthesis;
    (c) an internal structure within said outer membrane for supporting said outer membrane and cooperating with said soft, partially-deformable, elastic filler material to support said outer membrane and providing an enhanced life-like look and feel to the prosthesis; and
    (d) said internal structure having at least one first baffle extending between and connected to said front and rear portions, and at least one second baffle connected to said side portion, said at least one first and second baffles having at least one weephole and wherein said internal structure further has louvers attached to the interior of said outer membrane and to said first and second baffles, whereby said first and second baffles are disposed generally perpendicular to each other, said first baffle being connected with said second baffles thereby forming compartments in said enclosure.

2. The prosthesis of claim 1, wherein said filler material is selected from the group consisting of sponge rubber, foam rubber, silicone cylindrical, spherical, or polygonal beads, and silicone fibers in fluid suspension.

3. The prosthesis of claim 1, wherein said filler material is silicone beads further comprising solid randomized spheres.

4. The prosthesis of claim 1, wherein said filler material is silicone beads further comprising a combination of cylinders and solid randomized spheres.

5. The prosthesis of claim 1, wherein said filler material is fractured silicone pyramids and tetrahedrons.

6. An improved mammary prosthesis for implantation in humans comprising:
    (a) a soft, flexible outer membrane having front, rear, and side portions forming an enclosure for receiving a filler material;
    (b) a soft, partially-deformable, elastic filler material received within said outer membrane to support said outer membrane and provide an enhanced life-like look and feel to the prosthesis;
    (c) an internal structure within said outer membrane for supporting said outer membrane and cooperating with said soft, partially-deformable, elastic filler material to support said outer membrane and providing an enhanced life-like look and feel to the prosthesis;
    (d) said internal structure having at least one first baffle extending between and connected to said front and rear portions, and at least one second baffle connected to said side portion, whereby said first and second baffles are disposed generally perpendicular to each other, said first baffle being connected with said second baffle thereby forming compartments in said enclosure; and
    (e) said first and second baffles of said internal structure further having weep holes therethrough.

7. The prosthesis of claim 6, wherein said filler material is selected from the group consisting of sponge rubber, foam rubber, silicone cylindrical spherical, or polygonal beads, and silicone fibers in fluid suspension.

8. The prosthesis of claim 6, wherein said filler material is silicone beads further comprising solid randomized spheres.

9. The prosthesis of claim 6, wherein said filler material is silicone beads further comprising a combination of cylinders and solid randomized spheres.

10. The prosthesis of claim 6, wherein said filler material is fractured silicone pyramids and tetrahedrons.

11. An improved mammary prosthesis for implantation in humans comprising:
    (a) a soft, flexible outer membrane having front, rear, and side portions forming an enclosure for receiving a filler material;
    (b) a soft, partially-deformable, elastic filler material within said outer membrane;
    (c) an internal structure within said outer membrane for supporting said outer membrane and cooperating with said soft, partially-deformable, elastic filler material to support said outer membrane and providing an enhanced life-like look and feel to the prosthesis;
    (d) said internal structure having at least one first baffle extending between and connected to said front and rear portions, and at least one second baffle connected to said side portion, whereby said first and second baffles are disposed generally perpendicular to each other, said first baffle being connected with said second baffle thereby forming compartments in said enclosure; and
    (e) said internal structure further having louvers attached to the interior of said outer membrane.

12. The prosthesis of claim 11, wherein said filler material is selected from the group consisting of sponge rubber, foam rubber, silicone cylindrical, spherical, or polygonal beads, and silicone fibers in fluid suspension.

13. The prosthesis of claim 11, wherein said filler material is silicone beads further comprising solid randomized spheres.

14. The prosthesis of claim 11, wherein said filler material is silicone beads further comprising a combination of cylinders and solid randomized spheres.

15. The prosthesis of claim 11, wherein said filler material is fractured silicone pyramids and tetrahedrons.

16. An improved mammary prosthesis for implantation in humans comprising:
    (a) a soft, flexible outer membrane having front, rear, and side portions forming an enclosure for receiving a filler material;
    (b) a soft, partially-deformable, elastic filler material within said outer membrane to support said outer membrane and provide an enhanced life-like look and feel to the prosthesis, said filler material is selected from the group consisting of sponge rubber, foam rubber, silicone beads, and silicone fibers in fluid suspension;
    (c) an internal structure within said membrane for supporting said outer membrane and cooperating with said soft, partially deformable, elastic filler material to support said outer membrane and providing an enhanced, life-like look and feel to the prosthesis; and
    (d) said internal structure having at least one first baffle extending between and connected to said front and rear portions, and at least one second baffle connected to said side portion, said at least one first baffle being connected with said at least one second baffle thereby forming compartments in said internal structure, said at least one first and second baffles further having at least one weephole therethrough.

17. An improved mammary prosthesis for implantation in humans comprising:
(a) a soft, flexible outer membrane having front, rear, and side portions forming an enclosure for receiving a filler material;
(b) an internal structure within said membrane for supporting said outer membrane and providing an enhanced, life-like look and feel to the prosthesis;
(c) a soft, partially-deformable, elastic filler material received within said outer membrane and cooperating with said internal structure to support said outer membrane;
(d) said internal structure having at least one first baffle extending between and connected to said front and rear portions, and at least one second baffle connected to said side portion, whereby said first and second baffles are disposed generally perpendicular to each other, said first baffle being connected with said second baffle thereby forming compartments in said enclosure;
(e) said internal structure further having louvers attached to the interior of said outer membrane and to said first and second baffles; and
(f) said first and second baffles of said internal structure further having weep holes therethrough.

18. The prosthesis of claim 17, wherein said filler material is selected from the group consisting of sponge rubber, foam rubber, silicone cylindrical, spherical, or polygonal beads, and silicone fibers in fluid suspension.

19. The prosthesis of claim 17, wherein said filler material is silicone beads further comprising solid randomized spheres.

20. The prosthesis of claim 17, wherein said filler material is silicone beads further comprising a combination of cylinders and solid randomized spheres.

21. The prosthesis of claim 17, wherein said filler material is fractured silicone pyramids and tetrahedrons.

22. The prosthesis of claim 1, wherein said outer membrane has an enhanced, undulating, random sculptured, irregular, substantially smooth surface of peaks, valleys, slopes, and terraces without interstices disposed over at least a portion of said outer membrane.

23. The prosthesis of claim 22, wherein the average height differential between the peaks and valleys is in a range of about 800 mm to about 2500 mm.

24. The prosthesis of claim 6, wherein said outer membrane has an enhanced, undulating, random sculptured, irregular, substantially smooth surface of peaks, valleys, slopes, and terraces without interstices disposed over at least a portion of said outer membrane.

25. The prosthesis of claim 24, wherein the average height differential between the peaks and valleys is in a range of about 800 mm to about 2500 mm.

26. The prosthesis of claim 11, wherein said outer membrane has an enhanced, undulating, random sculptured, irregular, substantially smooth surface of peaks, valleys, slopes, and terraces without interstices disposed over at least a portion of said outer membrane.

27. The prosthesis of claim 26, wherein the average height differential between the peaks and valleys is in a range of about 800 mm to about 2500 mm.

28. The prosthesis of claim 16, wherein said outer membrane has an enhanced, undulating, random sculptured, irregular, substantially smooth surface of peaks, valleys, slopes, and terraces without interstices disposed over at least a portion of said outer membrane.

29. The prosthesis of claim 28, wherein the average height differential between the peaks and valleys is in a range of about 800 mm to about 2500 mm.

30. The prosthesis of claim 16, wherein said internal structure has at least one first baffle extending between and connected to said front and rear portions, and at least one second baffle connected to said side portion, whereby said first and second baffles are disposed generally perpendicular to each other, said first baffle being connected with said second baffle thereby forming compartments in said enclosure.

31. The prosthesis of claim 16, wherein said filler material is silicone beads further comprising solid randomized spheres.

32. The prosthesis of claim 16, wherein said filler material is silicone beads further comprising combination of cylinders and solid randomized spheres.

33. The prosthesis of claim 17, wherein said outer membrane has an enhanced, undulating, random sculptured, irregular, substantially smooth surface of peaks, valleys, slopes, and terraces without interstices disposed over at least a portion of said outer membrane.

34. The prosthesis of claim 33, wherein the average height differential between the peaks and valleys is in a range of about 800 mm to about 2500 mm.

35. The prosthesis of claim 6, wherein said internal structure has a plurality of first and second baffles aligned generally parallel to each other and has louvers attached to the interior of said outer membrane and to said first and second baffles.

36. The prosthesis of claim 11, wherein said first and second baffles contain at least one weep hole.

37. The prosthesis of claim 11, wherein said first and second baffles have louvers attached thereto.

* * * * *